United States Patent [19]

Albal et al.

[11] Patent Number: 5,171,868

[45] Date of Patent: Dec. 15, 1992

[54] EPOXIDATE TREATMENT

[75] Inventors: Rajendra S. Albal; Robert N. Cochran; T. Ben Hsu, all of West Chester, Pa.

[73] Assignee: ARCO Chemical Technology, L.P., Wilmington, Del.

[21] Appl. No.: 869,565

[22] Filed: Apr. 15, 1992

[51] Int. Cl.$^5$ ............... C07D 301/19; C07D 303/04; C07D 29/76; C07D 33/22

[52] U.S. Cl. .................... 549/529; 568/754; 568/758; 568/810; 568/815

[58] Field of Search .......................... 549/529

[56] References Cited

U.S. PATENT DOCUMENTS

| | | | |
|---|---|---|---|
| 3,351,635 | 11/1967 | Kollar | 260/348.5 |
| 3,418,340 | 12/1968 | Russell | 549/529 |
| 3,439,001 | 4/1969 | Pell et al. | 260/348.5 |
| 3,523,956 | 8/1970 | Kaplan | 549/529 |
| 3,536,732 | 10/1970 | Borchert et al. | 549/529 |
| 3,860,662 | 1/1975 | Kollar | 549/529 |
| 4,975,266 | 12/1990 | Albal et al. | 423/591 |

FOREIGN PATENT DOCUMENTS

| | | | |
|---|---|---|---|
| 56-39025 | 4/1981 | Japan. | |
| 7709128 | 2/1978 | Netherlands | 549/529 |
| 12327105 | 5/1971 | United Kingdom. | |

*Primary Examiner*—Joseph E. Evans
*Attorney, Agent, or Firm*—William C. Long

[57] ABSTRACT

Caustic requirements are substantially reduced in the treatment of epoxidate from olefin/ethylbenzene hydroperoxide epoxidation by treating the epoxidate products with an aqueous stream comprised of alkali metal carbonate, separating a phenol-containing 1-phenyl ethanol fraction from the treated expodiate, separating phenol from the 1-phenyl ethanol fraction by treatment with basic anion exchange resin, regenerating the resin with aqueous alkali metal hydroxide, and converting alkali metal hydroxide from the resin regeneration to alkali metal carbonate for use in the epoxidate treatment.

4 Claims, 1 Drawing Sheet

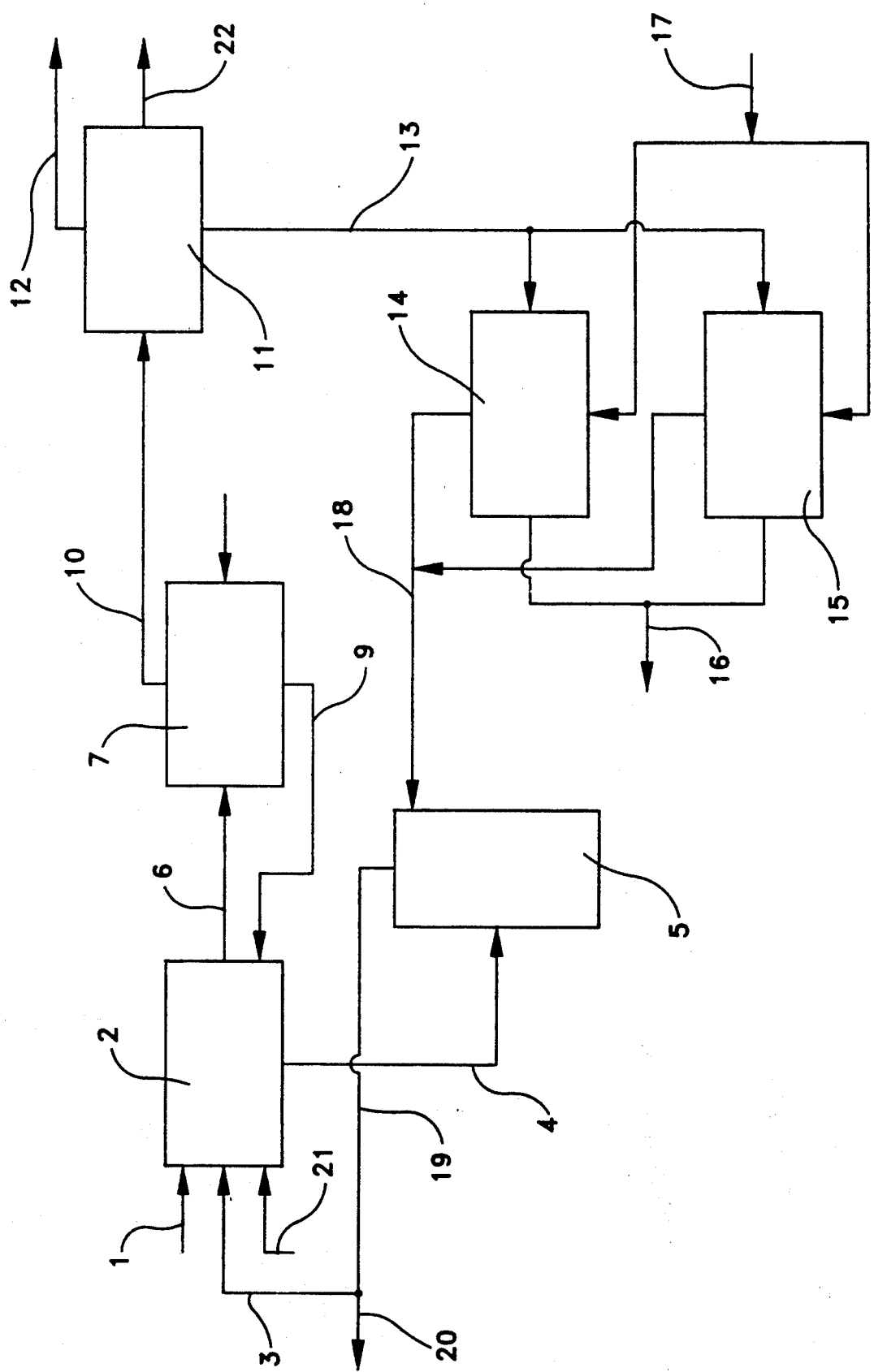

EPOXIDATE TREATMENT

BACKGROUND OF THE INVENTION

1. Field of the Invention

The present invention relates to an improved treatment of epoxidate such as that formed in the commercial propylene oxide / styrene monomer process whereby the amount of water employed in the treatment is substantially reduced, and the waste material which is formed and which must be disposed of is also substantially reduced.

2. Description of the Prior Art

An extremely successful process for the co-production of propylene oxide and styrene monomer involves the molecular oxygen oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol to styrene monomer. The basic patent describing this process is U.S. Pat. No. 3,351,635.

It is known to treat the epoxidate mixture, usually after separation of unreacted propylene, with aqueous sodium hydroxide. This treatment accomplishes neutralization of acidic materials, removal of soluble molybdenum catalyst and removal of phenols contained in the epoxidate. The neutralization of acidic materials is important in reducing corrosion problems which otherwise would be encountered in subsequent processing steps as well as in reducing product yield loss during subsequent distillations. The separation of catalyst is, of course, necessary, while the separation of phenols is important with regard to styrene monomer product quality and to avoid yield losses during the dehydration of 1-phenyl ethanol. Frequently, product styrene monomer is also treated with caustic in order to separate phenol which cannot readily be separated by distillation.

There are, however, problems associated with epoxidate treatment with aqueous caustic. At the high pH necessary for effective phenol removal, usually above 12, there is a significant epoxide yield loss as well as emulsification problems in decantation and problems of sodium carry over. Also, the disposal of large amounts of spent caustic solution represents a severe problem.

U.S. Pat. No. 3,439,001 shows treatment of recycle ethyl benzene with aqueous alkali in a propylene oxide / styrene monomer process.

U.S. Pat. No. 4,975,266 shows removal of phenol from 1-phenyl ethanol prior to oxidation to form hydrogen peroxide by treatment with basic anion exchange resins.

Japanese Patent Publication 56-39025 shows removing phenols from organic compounds by contact with polyvinyl pyridine resin.

U.K. Patent 1,232,710 shows the treatment of isobutane oxidate with aqueous alkali metal hydroxide or carbonate.

BRIEF DESCRIPTION OF THE INVENTION

In accordance with the present invention, an improved process is provided for the treatment of epoxidate such as that formed in a process for the co-production of propylene oxide and styrene monomer whereby problems associated with caustic treatment by prior procedures can be substantially avoided. Specifically, in accordance with the present invention, the epoxidate, preferably after removal of unreacted propylene, is contacted with an aqueous stream composed of alkali metal carbonate under conditions effective to neutralize acidic materials contained in the epoxidate and to separate the soluble molybdenum catalyst used in the epoxidation into the aqueous phase. The resulting mixture is phase separated and the treated epoxidate after water washing to remove alkali metal is separated by conventional procedures into the various components. The aqueous carbonate extract stream from the epoxidate treatment step is passed to a waste water incinerator or a wet air oxidation unit wherein aqueous alkali metal carbonate is regenerated. The treated epoxidate is resolved into the various product fractions including a fraction concentrated in 1-phenyl ethanol which comprises the feed to a dehydration unit for the production of styrene monomer. In accordance with the present invention, the phenol materials which are contained in this fraction and which are undesirable both from the standpoint of styrene monomer yields and purity are separated by treatment with a basic anion exchange resin. In this way contaminating phenols are removed from the 1-phenyl ethanol fraction prior to dehydration. The basic resin is periodically regenerated by passing aqueous alkali metal hydroxide therethrough. In accordance with the invention, the caustic stream from the resin regeneration can likewise be passed to the waste water incinerator or wet oxidation unit wherein the alkali metal hydroxide equivalent contained therein is converted to alkali metal carbonate, which material can then be employed in the initial epoxidate treatment step.

Through the specified combination of steps, the amount of spent caustic solution which must be purged and disposed of is substantially reduced with the concomitant improvements in the process economics and in the waste caustic disposal.

BRIEF DESCRIPTION OF THE DRAWING

The accompanying drawing illustrates in schematic form practice of the invention.

DETAILED DESCRIPTION

The practice of the present invention can best be described with reference to the accompanying drawing. The epoxidate stream resulting from homogeneous molybdenum catalyzed reaction between propylene and ethyl benzene hydroperoxide, after unreacted propylene is removed (not shown), passes via line 1 to contact zone 2. An aqueous stream comprised of alkali metal carbonate is introduced into zone 2 by means of line 3, and the streams are intimately admixed and separated into immiscible phases in zone 2. Alkali metal carbonate optionally together with some alkali metal hydroxide introduced via line 21 is provided in at least the amount needed to neutralize the acidic components of the epoxidate. As a result of this contact, the acidic impurities contained in the epoxidate are reacted with the alkali materials and removed in the aqueous phase along with the molybdenum catalyst. This aqueous phase passes via line 4 to wet oxidation or incinerator unit 5.

The conditions in zone 2 are maintained such that the aqueous phase has a relatively low pH, i.e. below 10, compared with 12–13 in the conventional aqueous caustic treatment. At such conditions, the organic acidic materials are effectively removed without significant yield loss of propylene oxide, without the formation of troublesome emulsions, and without substantial alkali metal carry over in the organic phase.

The aqueous stream introduced into zone 2 via line 3 can consist of aqueous alkali metal carbonate. However, sodium carbonate has only a modest solubility in water and in order to reduce the amount of water introduced into zone 2 via line 3, it is sometimes advantageous to supplement the alkali metal carbonate with alkali metal hydroxide which has a much greater water solubility. Care must be exercised, however, to ensure that the amount of alkali metal hydroxide introduced does not result in aqueous phase pH of 10 or more. Advantageously, aqueous alkali metal carbonate and aqueous alkali metal hydroxide (introduced via line 21) are fed to zone 2 in amounts so as to maintain the pH of the aqueous phase therein below 10 and preferably in the range of about 8–9.7.

The treated epoxidate passes from zone 2 by means of line 6 to wash and decantation zone 7 wherein the epoxidate is washed with water introduced by means of line 8 to remove contained alkali metal compounds. The lower aqueous phase passes from zone 7 by means of line 9 to alkali metal carbonate treatment zone 2 in order to aid in the contact and separation of the materials in zone 2.

The washed epoxidate, substantially free of alkali metal compounds, acids and molybdenum compounds, passes by means of line 10 to separation zone 11. Although zone 11 is represented by a single separation unit, it will be appreciated that in actual practice the treated epoxidate is appropriately separated by a series of distillate steps into component streams including a propylene oxide product stream, an ethyl benzene stream, and a stream concentrated in 1-phenyl ethanol for dehydration to produce styrene monomer. As indicated in the drawing, the propylene oxide stream is removed via line 12, the ethyl benzene stream via line 22, and the 1-phenyl ethanol stream is removed from separation zone 11 by means of line 13.

In accordance with the invention, there are provided anion exchange resin bed contact zones 14 and 15 which are designed to be used alternately. Specifically, while one zone is employed in the contact and removal of phenol compounds from the 1-phenyl ethanol stream, the other bed can be in the regeneration cycle for regeneration with aqueous alkali metal hydroxide. The contact with the anion exchange resin results in the effective removal of phenol and phenol derivatives, and the treated 1-phenyl ethanol stream passes via line 16 to a conventional dehydration zone for conversion to styrene monomer in accordance with known procedures. Aqueous caustic is introduced via line 17 and functions to regenerate the spent resin beds in accordance with well known technologies. The aqueous stream from the regeneration of the anion exchange beds passes via line 18 to incineration or wet oxidation zone 5 wherein it is incinerated in accordance with known procedures together with the aqueous alkali metal carbonate stream from contact zone 2. Aqueous alkali metal carbonate formed in zone 5 passes via line 19 with a portion being purged through line 20 and the remainder passing via line 3 for use in the treatment of epoxidate in zone 2.

As an alternative to the purge system shown, where the molybdenum compounds in line 19 are sufficiently insoluble, a filtration (not shown) can be partially or completely substituted for the purge in order to prevent molybdenum build-up.

The low pH, i.e. less than 10 of the alkali metal carbonate wash phase, compared with prior art strong caustic wash (pH > 12) reduces base-catalyzed propylene oxide losses to waste by-products by the order of 0.5% selectivity points, thus substantially improving process economics.

Carbonate and bicarbonate anions act as demulsifying agents for the emulsions observed in the epoxidate caustic wash. Whereas both organic and aqueous phases in the conventional epoxidate caustic wash are opaque emulsions, these phases in the epoxidate alkali metal carbonate wash process are translucent solutions. Eliminating emulsions from the wash steps improves process control and eliminates generation of emulsified rag layers in the wash decanters, which are disposed as process waste.

The lower pH and the elimination of emulsions with the carbonate wash result in reduced alkali metal compound carryover into the organic stream. This in turn reduces fouling of reboilers with alkali metal salts, and reduces alkali metal contamination of the heavies purge that is made downstream of the wash.

The anion exchange resin bed treatment in zones 14 and 15 removes as much as 80% of ethyl phenols in the stream as well as up to 100% of phenol. Ethyl phenols, which are made during the ethyl benzene oxidation to ethyl benzene hydroperoxide, are weaker acids than phenol, and are only 10% removed by the usual epoxidate caustic wash. Ethyl phenols cause increased styrene losses to heavies in the 1-phenyl ethanol dehydration step. Removing 80% of ethyl phenols before dehydration saves of the order of 0.6% overall styrene selectivity which further results in substantially improved process economics.

When combined with a wastewater oxidation unit as in FIG. 1, the process allows recycle of base as alkali metal carbonate solution to the epoxidate carbonate wash. Fresh caustic is used to regenerate the resin bed, where the reaction is stoichiometric, (1 equivalent caustic to extract 1 mole phenate or ethyl phenate anion). Overall, the process has the potential to reduce fresh caustic consumption by 65% compared with the conventional operations. There is also a corresponding 65% reduction in alkali metal carbonate solution that must be purged from the process.

The present process requires less water in the epoxidate carbonate wash for alkali metal removal compared with the conventional caustic wash. The potential wastewater reduction is 50%. This reduces the energy required to vaporize water in the wastewater oxidation unit.

Ion exchange resins which are employed in practice of the invention are basic anion exchange resins which are well known articles of commerce. Both strong-base resins and weak-base resins can be used.

Strong-base resins can be produced by the reaction between chlormethylated styrene-DVB copolymer and a tertiary amine such as trimethyl amine, which results in a resin with quaternary ammonium groups.

The principal types of weak-base anion exchangers are amine derivatives of styrene-DVB copolymers, epichlorohydrin-amine condensation products, and amine derivatives of phenol-formaldehyde products, and may contain primary, secondary or tertiary amine groups, or mixtures of some or all of these groups.

Weak-base styrene-DVB resins can be made, for example, by aminating chloromethylated copolymer in much the same way that strong-base styrene-DVB resins are made, except that primary or secondary amines are generally used instead of a tertiary amine.

U.S. Pat. Nos. which describe the preparation of basic anion resins useful in the present invention include: 4,025,467, 3,791,996, 3,817,878, 3,346,516, 4,082,701, 3,843,566, 3,813,353, 3,812,061, 3,882,053, 3,793,273, 3,296,233, 3,108,922, 3,005,786, 3,637,535 and 4,052,343.

The use of alkali metal carbonate where the alkali metal is sodium or potassium is preferred. Sodium carbonate has the advantage of being lower in cost while potassium carbonate has the important advantage of greater solubility in water.

A mixture of alkali metal carbonate with a minor amount of alkali metal hydroxide can be used in the epoxidate treatment step. The use of such mixtures has the advantage that the pH of the aqueous phase remains fairly low, below 10, thus avoiding emulsion problems and alkali metal carryover while the total amount of water added is minimized by virtue of the greater water solubility of the alkali metal hydroxide.

Epoxidates which are treated in accordance with the invention are those which are prepared by the known molybdenum catalyzed reaction of propylene with ethyl benzene hydroperoxide. U.S. Pat. No. 3,351,635 provides a full description of this reaction.

The reaction conditions which are employed in the epoxidation can vary quite broadly. As described in said patent, temperatures which can be employed can vary quite widely depending upon the reactivity and other characteristics of the particular system. Temperatures broadly in the range of about $-20°$ to $200°$ C., desirably $0°$ to $150°$ C., and preferably $50°-120°$ C., can be employed. The reaction is carried out at pressure conditions sufficient to maintain a liquid phase. Although sub-atmospheric pressures can be employed, pressures usually in the range of about atmospheric to about 1,000 psig are most desirable.

In the oxidation of the olefinic substrate, the ratio of substrate to organic peroxy compounds can vary over a wide range. Generally, mol ratios of olefinic in the substrates to hydroperoxide broadly in the range of 0.5:1 to 100:1, desirably 1:1 to 20:1 and preferably 2:1 to 10:1 are employed.

The concentration of hydroperoxides in the substrate oxidation reaction mixture at the beginning of the reaction will normally be one percent or more although lesser concentrations will be effective and can be used.

The substrate oxidation reaction can be carried out in the presence of a solvent, and in fact, it is generally desirable that one be used. In general, aqueous solvents are not contemplated. Among the suitable substances are hydrocarbons, which may be aliphatic, naphthenic or aromatic, and the oxygenated derivatives of these hydrocarbons. Preferably, the solvent has the same carbon skeleton as the hydroperoxide used, so as to minimize or to avoid solvent separation problems. Ethylbenzene is a preferred solvent.

It is generally advantageous to carry out the reaction to achieve as high a hydroperoxide conversion as possible, consistent with reasonable selectivities. Reaction times ranging from a minute to many hours, preferably about 10 minutes to 10 hours are suitable, while 20 minutes to 3 hours are usually employed.

EXAMPLE

Referring to the accompanying drawing, an epoxidate stream from the molybdenum catalyzed reaction of propylene with ethyl benzene hydroperoxide, after removal of unreacted propylene, passes via line 1 to zone 2 at the rate of 1000 lbs. per hr. The epoxidate stream comprises about 8 wt. % propylene oxide, about 30 wt. % 1-phenyl ethanol, about 53 wt. % ethyl benzene, about 4 wt. % acetophenone, about 1600 ppm phenol and 700 ppm ethyl phenols, about 0.34 wt. % acids, and about 50 ppm Mo.

Aqueous sodium carbonate (10 wt. % sodium carbonate) passes to zone 2 via line 3 at the rate of 67 lbs./hr. An aqueous wash stream from zone 7 passes via line 9 to zone 2 at the rate of 33 lbs./hr. Conditions in zone 2 are a temperature of 35° C. and normal pressure.

The streams are admixed and phase separated in zone 2. The lower aqueous phase passes via line 4 to wet incinerator 5 at the rate of 100 lbs./hr. This stream has a pH of about 9.5 and a composition of about 3.3 wt. % sodium carbonate, small amounts of organics and contains most of the molybdenum from the organic feed stream.

The organic phase containing 40 ppm Na passes from zone 2 via line 6 to wash zone 7 at the rate of 1000 lbs./hr. In zone 7 the organic phase is washed with water which is introduced via line 8 at the rate of 33 lbs./hr. Conditions in zone 7 are 35° C. and normal pressure.

The aqueous phase from zone 7 passes via line 9 to zone 2 at 33 lbs./hr. as above indicated while the organic phase passes from zone 7 via line 10 to separation zone 11. This organic phase contains 20 ppm Na and comprises about 7.5 wt. % propylene oxide, about 30 wt. % 1-phenyl ethanol, about 53 wt. % ethyl benzene, about 4 wt. % acetophenone, and about 0.23 wt. % phenols. Acid content has been reduced to less than 250 ppm and molybdenum content to 0.5 ppm Mo.

Separation zone 11 actually comprises a series of distillation columns. In a first distillation, product propylene oxide is distilled overhead at 42° C. and 36.7 psig and recovered at the rate of 75 lbs./hr. and ethyl benzene is recovered via line 22 at the rate of about 525 lbs./hr.

Bottoms at 134° C. and 41.1 psig is passed through several distillation columns at the rate of 400 lbs./hr. via line 13 (after cooling) to ion exchange resin treatment zone 14. In zone 14 the organic stream passes through a bed of strong bases anion exchange resin such as Rohn & Haas Amberlyst A-26 at 35° C. and is recovered therefrom via line 16. As a result of the resin treatment, 90% of the phenol and 80% of the ethyl phenols are removed from the organic stream. The treated organic stream from zone 14 comprises about 84 wt. % 1-phenyl ethanol, about 12 wt. % acetophenone and about 4 wt. % others and passes (not shown) to a conventional procedure for styrene monomer production.

Zone 15, which is packed with the same resin as zone 14, is regenerated by contact with aqueous caustic while zone 14 is being used to remove phenols. Aqueous caustic (5 wt. % NaOH) passes via line 17 to zone 15 at the rate of 66 lbs./hr. Regeneration temperature is 35° C. and the regeneration contact is continued until phenols are removed from the resin.

The caustic regeneration stream passes via line 18 to wet incinerator 5. When regeneration is complete, zone 15 is maintained on stand-by until the phenol removal capability of zone 14 has been reduced to a predetermined extent and at that point stream flows are switched by conventional means such that zone 15 becomes the phenol removing zone and zone 14 undergoes regeneration as above described.

Wet incineration zone is operated in conventional fashion to oxidize organic materials fed thereto in the aqueous streams passing via lines 4 and 18. Wet incineration conditions are about 1000° C. and 180 psig, air is employed as oxidant (not shown). In zone 5, the sodium materials are converted to sodium carbonate. The sodium carbonate stream is removed via line 19 at the rate of 80 lbs./hr. and comprises 10 wt. % sodium carbonate. About 13 lbs./hr. are purged and the remainder is recycled via line 3 to sodium carbonate treatment zone 2.

We claim:

1. In a process for the epoxidation of an olefin with ethylbenzene hydroperoxide, the improvement which comprises:
   a) contacting the epoxidate product mixture comprised of 1-phenyl ethanol, epoxide and acidic and phenol impurities from the epoxidation with aqueous alkali metal carbonate at conditions effective to neutralize acidic components of the epoxidate mixture,
   b) separating an organic epoxidate phase from an aqueous alkali metal carbonate phase,
   c) separating a phenol-containing 1-phenyl ethanol fraction from the treated epoxidate,
   d) removing phenol from the 1-phenyl ethanol fraction by contact with a basic anion exchange resin,
   e) regenerating deactivated basic anion exchange resin by contact with aqueous alkali metal hydroxide solution,
   f) combining aqueous alkali metal hydroxide solution from resin regeneration step e) and aqueous alkali metal carbonate from step b) and regenerating aqueous alkali carbonate therefrom for use in step a).

2. The process of claim 1 wherein the alkali metal is sodium.

3. The process of claim 1 wherein the alkali metal is potassium.

4. The process of claim 1 wherein the epoxide is propylene oxide.

* * * * *